(12) United States Patent
Vandervorst

(10) Patent No.: US 6,809,317 B2
(45) Date of Patent: Oct. 26, 2004

(54) METHOD AND APPARATUS FOR LOCAL SURFACE ANALYSIS

(75) Inventor: Wilfried Vandervorst, Mechelen (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 0 days.

(21) Appl. No.: 10/313,945

(22) Filed: Dec. 6, 2002

(65) Prior Publication Data

US 2003/0127591 A1 Jul. 10, 2003

(30) Foreign Application Priority Data

Dec. 6, 2001 (EP) ............................................ 01870272

(51) Int. Cl.$^7$ .............................................. H01J 49/10
(52) U.S. Cl. ................ 250/288; 204/192 E; 204/192 R
(58) Field of Search ................................. 250/288, 282, 250/287, 423 P, 281, 492.3; 204/192 E, 192 R, 298

(56) References Cited

U.S. PATENT DOCUMENTS 3,567,927 A * 3/1971 Barrington .................. 250/282
4,496,449 A * 1/1985 Rocca et al. ............. 204/298.36
4,733,073 A * 3/1988 Becker et al. ............... 250/288

* cited by examiner

Primary Examiner—John R. Lee
Assistant Examiner—Zia R. Hashmi
(74) Attorney, Agent, or Firm—Knobbe Martens Olson & Bear LLP

(57) ABSTRACT

The present invention is related to a method and apparatus for performing a surface analysis of a sample by mass spectrometry. According to one aspect of the invention, the ions necessary for the spectrometry are produced by a probe beam, which is preferably an electron beam, in combination with a gas mixture comprising at least a reactive gas component. Due to the interaction of the probe beam with the reactive gas and the surface atoms, reactions take place between the surface atoms and the reactive gas molecules, resulting in volatile compounds being released from the surface. One or more laser beams cause the ionization of these compounds, after which the resulting ions are accelerated towards a mass spectrometer. The method and apparatus allow an accurate depth profiling of a test sample to be performed.

22 Claims, 1 Drawing Sheet

METHOD AND APPARATUS FOR LOCAL SURFACE ANALYSIS

BACKGROUND OF THE INVENTION

1. Field of the Invention

The present invention is related to a method and apparatus for surface diagnostics of substrates, in particular substrates used in the production of integrated circuit devices.

2. Description of the Related Technology

The known techniques for mass spectrometry include the Secondary Ion Mass Spectrometry (SIMS) method. This method uses an ion beam directed at a sample under investigation, which sputters a quantity of neutral and ionized matter from the sample's surface. The ions that are formed are then accelerated towards a mass spectrometry device.

Like many other techniques, SIMS is a method which disrupts the atomic structure of the sample. This makes it unadapted for the so-called 'depth-profiling', which is a measurement of the sample's composition as a function of depth. Accurate depth profiling is performed 'layer by layer', the thickness of each layer being as close as possible to the dimensions of one atom (near atomic accuracy). The important thing is to be able to free atoms in the layer closest to the surface, without disrupting atoms lying underneath the top layer. Current methods are not capable of performing depth profiling on a near atomic level of accuracy.

U.S. Pat. No. 4,733,073 describes a method and apparatus wherein a probe beam, such as an ion beam, an electron beam or a laser beam is directed at the sample under high vacuum. In a region close to the impact of the probe beam, the sputtered samples are ionized by non-resonant photo-ionization which allows a non-selective analysis of species present in the sample. This document speaks of regulating the probe beam's intensity in order to perform depth-profiling. Other methods have been described such as the Floating LowEnergy Ion Gun technique (FLIG®), described in the document 'An ultra-low energy ion column for sputter profiling' by M. G. Dowsett et al., proceedings of the Tenth International Conference on Secondary Ion Mass Spectrometry (SIMS X), Munster, Germany, Oct. 1–6, 1995. This last method has the objective to reduce the probe beam's energy down to 200 eV, in order to perform depth profiling. However, even at low energy level, the disruption of the atomic structure remains a problem when using ion beam technology.

The use of a laser as the probe beam, such as mentioned in U.S. Pat. No. 4,733,073 has the effect of ablation, i.e., wearing away parts of a sample by heating and subsequent evaporation or sublimation of the sample. This reaction can never be controlled so that it will only affect a top layer of atoms. A laser is therefore not suited for an accurate depth profiling.

Low energy electron beams are incapable of producing sufficient energy to release atoms from a sample. Increasing their energy will cause heat effects similar to the ones caused by laser beams.

Besides accurate depth profiling, higher demands are presently made in terms of the size of the analysed area on the sample surface, meaning that ever smaller areas, in particular areas of less than 1 $\mu m^2$ are becoming currently accessible. The current way of handling this problem is using ion beam technology by reducing the ion beam diameter, which invariably necessitates increasing the beam energy. This led to the development of high energy beams, such as used in the known Focused Ion Beam (FIB®) technique, described in 'The integration of a high performance quadrupole SIMS facility with a Ga+ LMIS based FIB Instrument', T. Dingle et al., proceedings of the Tenth International Conference on Secondary Ion Mass Spectrometry (SIMS X), Münster, Germany, Oct. 1–6, 1995. It is clear that this increased beam energy is detrimental to the preservation of atomic structures, as required for accurate depth profiling.

SUMMARY OF CERTAIN INVENTIVE ASPECTS

One aspect of the invention provides a method which allows accurate analysis of the composition of a sample, including depth profiling at near atomic level.

Another aspect of the invention provides a method which, in combination with the depth profiling, allows the analysis of areas smaller than 1 $\mu m^2$.

Another aspect of the invention is related to a method for performing a surface analysis of a sample. The method comprises placing a sample having a surface in an enclosure in which a low pressure is present, providing a gas mixture in close proximity with the surface, the mixture comprising one or more reactive gases, and applying a probe beam on a location of the surface so as to create an etching on the location. The method also comprises ionizing an etching product which is originated from the location of the surface so as to generate at least one ion, accelerating the at least one ion towards a mass spectrometer, and performing a mass spectrometry analysis on the at least one ion in the mass spectrometer.

Still another aspect of the invention provides an apparatus for performing a surface analysis of a sample. The apparatus comprises an enclosure, a gas mixture introducing portion, a maintaining portion, a probe beam provider, a laser beam provider, an accelerating portion and a mass spectrometer. The enclosure contains a sample having a surface. The gas mixture introducing portion introduces a gas mixture into the enclosure. The maintaining portion maintains the gas mixture in a predefined condition at close proximity to the surface. The probe beam provider provides a probe beam at a predefined location on the surface of the sample so as to create an etching on the location. The laser beam provider provides at least one laser beam to an etching product released from the location so as to produce at least one ion. The accelerating portion accelerates the at least one ion. The mass spectrometer performs a mass spectrometry on the accelerated at least one ion.

Yet another aspect of the invention provides a method of performing a surface analysis of a sample. The method comprises providing a gas mixture near a surface of the sample, the mixture comprising one or more reactive gases and applying a probe beam on a location of the surface such that the interaction between the probe beam, the gas mixture and the sample surface takes place and results in a compound being released from the surface. The method comprises ionizing the compound so as to generate at least one ion and performing a mass spectrometry analysis on the at least one ion.

DETAILED DESCRIPTION OF CERTAIN INVENTIVE EMBODIMENTS

Figure 1:
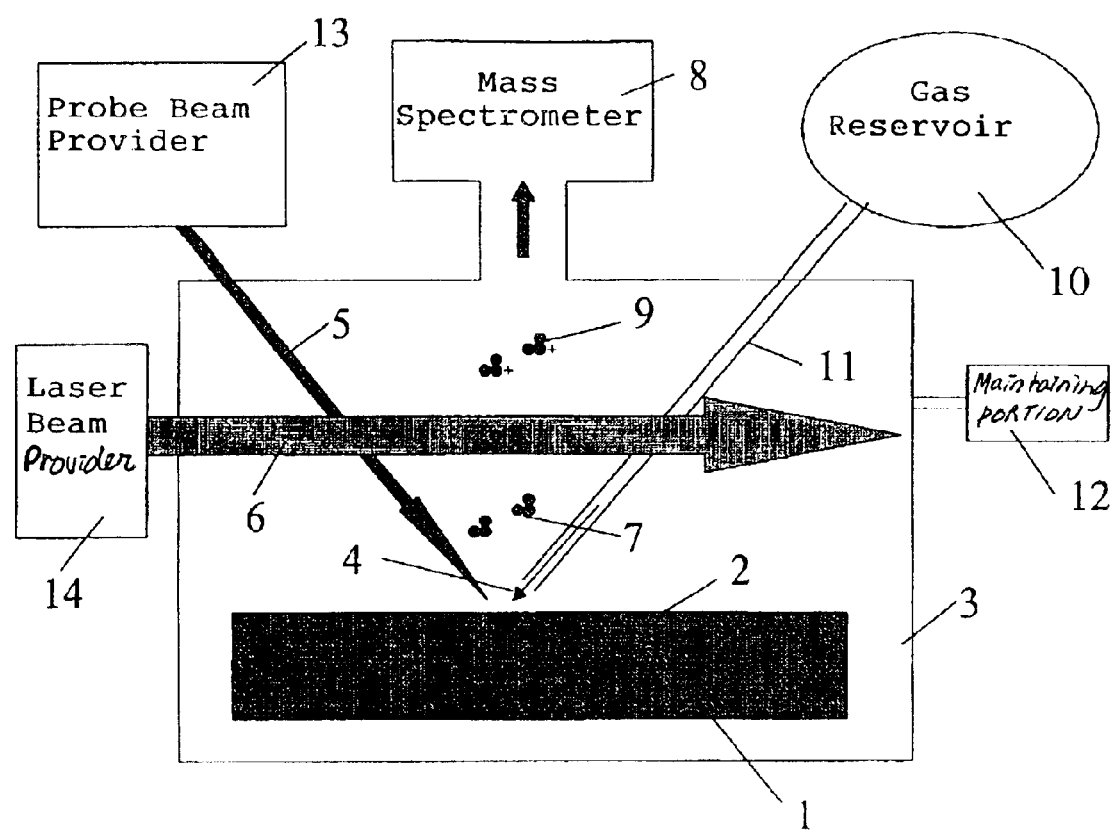
FIG. 1 represents a schematic view of the method and apparatus according to one aspect of the invention.

With reference to FIG. 1, a method for performing a surface analysis of a sample according to one aspect of the invention will be described. The method comprises placing a sample 1 having a surface 2, in an enclosure 3 where a low pressure is present, and bringing a gas mixture 4 in close proximity with the surface 2, the mixture 4 comprising one or more reactive gases, and preferably also a non-reactive buffer gas. The method also comprises applying a probe beam 5 on a location on the surface 2, thereby causing an etching to take place at the location, due to the interaction between the probe beam 5, the gas mixture 4 and the sample surface 2. The method comprises ionizing by the use of at least one laser beam 6, the etching products 7, originating from the location of the surface 2, and accelerating ions 9 resulting from the ionization procedure towards a mass spectrometer 8, and performing a mass spectrometry analysis on the ions 9.

In order to place the invention in the proper perspective, it is useful to look at the fundamental properties of particle beams, used in the prior art so far, which are mainly ion beams. There are basically two ways in which a particle of the probe beam may exchange energy with the atoms of the test sample. In the 'electronic energy exchange', the energy is received by the electrons of the sample atoms. The effect is that these electrons move to a higher energy level, but the atom itself is not displaced. The other type of energy exchange is 'nuclear energy exchange' wherein kinetic energy from incoming ions is transferred to substrate atoms through actual collisions. These collisions may release a number of atoms from the sample (=sputtering), but will also cause a cascade phenomenon, wherein atoms in the sample, notably atoms in layers underneath the surface layer, are disrupted.

In all known ion beam techniques, the 'nuclear energy exchange' is what takes place in order to produce the atoms for subsequent analysis. It must be clear however, that the ensuing cascades are detrimental for an accurate depth profiling. Lowering the ion beam energy will merely reduce the depth to which incoming ions may penetrate, but it will not rule out the cascading phenomenon.

Low energy electron beams generally produce particles with a low kinetic energy due to the low mass of the electrons. These beams are only capable of causing an 'electronic energy exchange', which is insufficient for actually releasing atoms from the substrate surface.

The technique of particle beam assisted etching is known. This has been described as an etching technique, for example, in U.S. Pat. No. 4,496,449. An electron beam (e-beam) induces the dissociation of molecules of the gases that are adsorbed onto the surface. Dissociated compounds then react with the surface molecules to form volatile products which are removed from the surface. The etching speed of this etching technique is sufficiently high, allowing a high removal rate, even for high thicknesses. The pressures used during etching in the vicinity of the sample are typically lower than $10^{-7}$ Pa.

In one aspect of the invention, the etching effect of the probe beam, which is preferably a low energy particle beam, in combination with a reactive gas, is used not for etching a pattern on the surface of the sample, but for releasing compounds from a test surface on the sample, which are ready for ionization and subsequent mass spectrometry. Compared to existing analysis techniques, this has a number of advantages. First of all, a low energy beam is used, preferably an electron beam, which causes virtually no disruption of the atomic structure.

The effect of the e-beam is to help the dissociation of the gases adsorbed to the surface and to allow the resulting products to react with the surface atoms. The e-beam causes the already mentioned 'electronic energy exchange', i.e., an exchange wherein electrons of the sample atoms are moved to a higher energy level. This fails to dislodge the atoms from the substrate, but it does put them in a state wherein they are more likely to form compounds with other atoms. This is where the reactive gas enters the equation: the dissociated gas compounds react with the 'excited' surface atoms, forming reaction products which are then released from the substrate for subsequent analysis.

This mechanism for producing compounds for ionization is fundamentally different from the sputtering of compounds by bombarding the sample with 'heavy' ions. The e-beam assisted etching allows for a localized reaction in terms of surface and in terms of depth. The depth profiling with this technique is accurate to near atomic level, because of the low energy of the e-beam, and because only the sample atoms which are in contact with the reactive gas can take part in the reactions for producing compounds for ionization. Underlying atoms therefore remain unaffected by the beam, so a layer-by-layer depth profiling may be performed.

The accuracy in terms of surface is expressed in the very small areas which can be analysed with the technique of the invention. This is due to the fact that e-beams can be focused to very small diameters, even at low energy. Defocusing of a particle (ion or electron) beam takes place due to a repulsion of particles of the same charge in the beam. Increasing the beam energy counters this effect. In the case of ion beams, this leads to excessively high beam energy levels which prohibit acceptable depth profiling. E-beams tend to defocus only at very low energy levels, so at normal energy levels, the beam is still sufficiently focused. According to a preferred embodiment, about an 1 keV electron beam is used, having a diameter of the order of about 5 nm, which is sufficient to study a test area of down to about 200 nm square, with an adequate resolution.

In one embodiment of the invention, $CF_4$ or $XeF_2$ are used as the reactive component in the mixture of gases. In the case of $CF_4$ used on a silicon substrate, dissociation and reaction eventually lead to the formation of gaseous $SiF_4$ molecules, which leave the sample surface. $O_2$ may be added to the gas mixture in order to prevent etching of the sample by the gas mixture itself, i.e., without a low energy beam being applied. It is found that in some cases, the oxidation of the sample surface after addition of $O_2$, causes this spontaneous etching to stop. $O_2$ may also be useful to remove C-atoms which are left on the surface after the above mentioned reactions. This removal of C takes place through formation and subsequent removal of $CO_2$.

In order to define the area of the sample surface that is to be analysed, a 'rastering' of the low energy beam is performed. According to a preferred embodiment of the invention, the low energy beam as well as the laser beam for ionization work in a pulsed mode. It is therefore important to synchronize the functioning of both beams. The rastering method which is preferably used selects a 'rastering surface', of which the central part is the actual area of analysis. Just before each laser beam pulse, the low energy beam pulse is directed at this central part, while in between laser beam pulses, the beam is directed at the surrounding parts, thereby creating a crater around the central part. The removal of the material around the central part is necessary to maintain a flat surface on this central part, during the deepening of the crater. The pulsed character of the low energy beam makes sure that only compounds coming from the central part are ionized by the laser beam.

The laser used for this purpose preferably directs one or more beams parallel to the sample surface. The ionisation can be accomplished using a resonant as well as a nonresonant process. According to a preferred embodiment, a non-resonant multiphoton ionisation process is induced with a focused laser beam or beams having a high intensity (order of $10^{10}$ W/cm2).

The low energy particle beam itself is preferably an electron beam or a photon beam. A common characteristic of all low energy beams used in the method of the invention, is that they cause essentially no 'nuclear energy exchange' with atoms of the test sample, but only 'electronic energy exchange'. This means that beams used in the invention do not cause a sputtering effect.

The detection of the ions produced by ionisation may be done by the known techniques, for example employing an electron multiplier and a Faraday cup.

Another aspect of the invention is related to an apparatus for performing the method of the invention. The elements of such an apparatus are illustrated in FIG. 1. The apparatus comprises an enclosure 3, an introducing portion 10, 11, a maintaining portion 12, a probe beam provider 13, a laser beam provider 14, an extracting portion (not shown), and a mass spectrometer 8. The enclosure 3 can contain a sample 1 having a surface 2. The introducing portion 10, 11 introduces a gas mixture 4 into the enclosure 3. The maintaining portion 12 maintains the gas mixture 4 in a predefined condition at close proximity to the sample 1. The probe beam provider 13 directs a low energy particle beam 5 at a predefined location on the surface 2 of the sample 1. The laser beam provider 14 directs one or more laser beams 6 substantially parallel to the surface 2. The extracting portion extracts ions 9, formed after ionization of products 7 resulting from the etching process. The mass spectrometer 8 performs mass spectrometry on the products 7.

The introducing portion may include a gas reservoir 10 and one or more gas tubes 11 for bringing the mixture 4 from the reservoir 10 towards the sample surface 2. The probe beam provider 13 may comprise an electron gun. The maintaining portion 12 may comprise a vacuum pump and valves, regulators and nozzles or the like for maintaining a low pressure inside the enclosure 3.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

What is claimed is:

1. A method of performing a surface analysis of a sample, comprising:
   placing a sample having a surface in an enclosure in which a low pressure is present;
   providing a gas mixture in close proximity with the surface, the mixture comprising one or more reactive gases;
   applying a probe beam on a location of the surface so as to create an etching on the location;
   ionizing an etching product which is originated from the location of the surface so as to generate at least one ion;
   accelerating the at least one ion towards a mass spectrometer; and
   performing a mass spectrometry analysis on the at least one ion in the mass spectrometer.

2. The method of claim 1, wherein the probe beam comprises an electron beam.

3. The method of claim 2, wherein the electron beam comprises an about 1 keV electron bean having a diameter of about 5 nm.

4. The method of claim 1, wherein the probe beam comprises a photon beam.

5. The method of claim 1, wherein the gas mixture comprises $CF_4$ or $XeF_2$.

6. The method of claim 1, further comprising adding $O_2$ to the gas mixture.

7. The method of claim 1, wherein the gas mixture further comprises a non-reactive buffer gas.

8. The method of claim 1, wherein the etching results from the interaction between the probe beam, the gas mixture and the sample surface.

9. The method of claim 1, wherein the ionizing comprises directing at least one laser beam above the surface.

10. The method of claim 1, wherein the probe beam is operated in a pulsed mode.

11. The method of claim 1, wherein the probe beam follows a rastering pattern on an area of the surface.

12. The method of claim 1, wherein at least one of the applying of the probe beam, the ionizing the etching product, and the accelerating of the at least one ion occurs repeatedly over a plurality of locations on the area of the surface.

13. An apparatus for performing a surface analysis of a sample, comprising:
    an enclosure configured to contain a sample having a surface;
    a gas mixture introducing portion configured to introduce a gas mixture into the enclosure;
    a maintaining portion configured to maintain the gas mixture in a predefined condition at close proximity to the surface;
    a probe beam provider configured to provide a probe beam at a predefined location on the surface of the sample so as to create an etching on the location;
    a laser beam provider configured to provide at least one laser beam to an etching product released from the location so as to produce at least one ion;
    an accelerating portion configured to accelerate the at least one ion; and
    a mass spectrometer configured to perform a mass spectrometry on the accelerated at least one ion.

14. The apparatus of claim 13, further comprising an extractor configured to extract the produced at least one ion.

15. The apparatus of claim 13, wherein the probe beam comprises a low energy particle beam.

16. The apparatus of claim 13, wherein the laser beam provider is configured to provide the at least one laser beam substantially parallel to the surface.

17. The apparatus of claim 13, wherein the gas mixture introducing portion comprises:
    a gas reservoir containing the gas mixture; and
    at least one gas tube configured to pass the gas mixture from the reservoir toward the sample surface.

18. The apparatus of claim 13, wherein the maintaining portion is configured to maintain a low pressure inside the enclosure.

19. The apparatus of claim 18, wherein the maintaining portion comprises one of the following: a vacuum pump, valve, regulator or nozzle.

20. A method of performing a surface analysis of a sample, comprising:

providing a gas mixture near a surface of the sample, the mixture comprising one or more reactive gases;

applying a probe beam on a location of the surface such that the interaction between the probe beam, the gas mixture and the sample surface takes place and results in a compound being released from the surface;

ionizing the compound so as to generate at least one ion; and performing a mass spectrometry analysis on the at least one ion.

21. An apparatus for performing a surface analysis of a sample, comprising:

a gas mixture providing portion configured to provide a gas mixture near a surface of the sample, the mixture comprising one or more reactive gases;

a probe beam provider configured to provide a probe beam on a location of the surface such that the interaction between the probe beam, the gas mixture and the sample surface takes place and results in a compound being released from the surface;

a laser beam provider configured to provide at least one laser beam to the compound so as to generate at least one ion; and a mass spectrometer configured to perform a mass spectrometry analysis on the at least one ion.

22. An apparatus for performing a surface analysis of a sample, comprising:

means for providing a gas mixture near a surface of the sample, the mixture comprising one or more reactive gases;

means for applying a probe beam on a location of the surface such that the interaction between the probe beam, the gas mixture and the sample surface takes place and results in a compound being released from the surface;

means for ionizing the compound so as to generate at least one ion; and means for performing a mass spectrometry analysis on the at least one ion.

* * * * *

UNITED STATES PATENT AND TRADEMARK OFFICE
CERTIFICATE OF CORRECTION

PATENT NO. : 6,809,317 B2
DATED : October 26, 2004
INVENTOR(S) : Wilfried Vandervorst Page 1 of 1

It is certified that error appears in the above-identified patent and that said Letters Patent is hereby corrected as shown below:

<u>Title page,</u>
Item [56], References Cited, U.S. PATENT DOCUMENTS, insert the following:
-- 4,393,311   7/1983   Feldman et al.   250/459.1
   5,272,338  12/1993   Winograd et al.  250/309
   6,204,189   3/2001   Petersen et al.  438/706 --.
Insert the following:
-- OTHER PUBLICATIONS
Benninghoven et al., "Surface MS: Probing Real-World Samples," *Analytical Chemistry*, July 1993, vol 65, no. 14, pages 630A-640A.
Migeon et al., "Ion microscope and ion microprobe analysis under oxygen, cesium and gallium bombardment," *International Journal of Mass Spectrometry and Ion Processes, May 1995, vol.* 143, pages 51-63 (1995).
Wood et al., "Imaging with Ion Beams and <u>Laser Positionizaiton</u>," *Analytical Chemistry, August 1994* vol. 66, no. 15, pages 2425-2432. --, Signed and Sealed this Thirtieth Day of May, 2006

JON W. DUDAS
*Director of the United States Patent and Trademark Office*